(12) United States Patent
Liu

(10) Patent No.: US 12,312,407 B2
(45) Date of Patent: May 27, 2025

(54) UNIVERSAL T CELLS AND THE METHOD OF USE THEREOF

(71) Applicant: ST PHI THERAPEUTICS CO., LTD., Zhejiang (CN)

(72) Inventor: Lingfeng Liu, Seattle, WA (US)

(73) Assignee: ST PHI THERAPEUTICS CO., LTD., Hangzhou (CN)

( * ) Notice: Subject to any disclaimer, the term of this patent is extended or adjusted under 35 U.S.C. 154(b) by 351 days.

(21) Appl. No.: 17/164,834

(22) Filed: Feb. 1, 2021

(65) Prior Publication Data

US 2021/0253712 A1   Aug. 19, 2021

Related U.S. Application Data

(60) Provisional application No. 62/968,071, filed on Jan. 30, 2020.

(51) Int. Cl.
| | | |
|---|---|---|
| *C07K 16/28* | (2006.01) | |
| *C07K 14/005* | (2006.01) | |
| *C07K 14/705* | (2006.01) | |
| *C07K 14/725* | (2006.01) | |

(52) U.S. Cl.
CPC ........ *C07K 16/2833* (2013.01); *C07K 14/005* (2013.01); *C07K 14/7051* (2013.01); *C07K 14/70517* (2013.01); *C07K 14/70521* (2013.01); *C07K 14/7056* (2013.01); *C07K 14/70578* (2013.01); *C07K 16/2809* (2013.01); *C07K 2317/522* (2013.01); *C07K 2317/524* (2013.01); *C07K 2317/526* (2013.01); *C07K 2317/53* (2013.01); *C07K 2317/622* (2013.01); *C07K 2319/02* (2013.01); *C07K 2319/03* (2013.01); *C07K 2319/30* (2013.01); *C12N 2710/16122* (2013.01)

(58) Field of Classification Search
CPC .............. C07K 16/2833; C07K 14/005; C07K 14/7051; C07K 14/70517; C07K 14/70521; C07K 14/7056; C07K 14/70578; C07K 16/2809; C07K 2317/522; C07K 2317/524; C07K 2317/526; C07K 2317/53; C07K 2317/622; C07K 2319/02; C07K 2319/03; C07K 2319/30; C07K 14/70539; C07K 14/71; C07K 2317/70; C07K 2319/00; C12N 2710/16122; C12N 2710/10322; C12N 2740/16022
See application file for complete search history.

(56) References Cited

U.S. PATENT DOCUMENTS

| | | | | |
|---|---|---|---|---|
| 10,287,354 B2 * | 5/2019 | Brogdon | ................. | A61P 35/00 |
| 10,570,186 B2 * | 2/2020 | Cooper | ............ | C07K 14/70521 |
| 2018/0148506 A1 * | 5/2018 | Png | ................ | A61K 39/001129 |

FOREIGN PATENT DOCUMENTS

| | | | | |
|---|---|---|---|---|
| JP | 2019502101 A | * | 1/2019 | ................ A61P 9/00 |
| WO | WO-2018193394 A1 | * | 10/2018 | ............. A61K 35/17 |

OTHER PUBLICATIONS

Leo et. al. Proc. Natl. Acad. Sci. 84:1374-1378 (1987) (Year: 1987).*
Yang et. al. Curr Opin Hematol. 22(6):509-515 (2015) (Year: 2015).*
Almagro et. al., Front. Immunol. 2018; 8:1751 (Year: 2018).*
Chiu et al., Antibodies, 8(55):1-80. (2019) (Year: 2019).*
Maciocia et. al. Blood. 132(1):700. (2018) (Year: 2018).*
Tokarew et. al. British Journal of Cancer 120:26-37 (2019) (Year: 2019).*
Conrad et. al. Cytometry Part A. 71A:925-933. (2001) (Year: 2001).*
Marvin et. al., Biochemistry, 42(23):7077-7083 (2003) (Year: 2003).*

* cited by examiner

*Primary Examiner* — Meera Natarajan
*Assistant Examiner* — Francesca Edgingtongiordan
(74) *Attorney, Agent, or Firm* — Junhe Law Office P.C.; James J. Zhu

(57) ABSTRACT

A series of recombinant DNA constructs and a method is disclosed for use in immunological therapy in general; and in disrupting T cell receptor (TCR), human leukocyte antigens (HLA) class I and NKG2D (Natural-Killer Group 2, member D) ligand expression in particular, with the effect of producing highly compatible autologous universal T cells for further genetically engineering for allogeneic administration. A Universal T (UT) construct is provided and used, comprising a TCR antibody fragment fused to a transmembrane domain (TMD) and ER retention domain of adenovirus early region 3 glycoprotein E3-19k (E3/19K) (TCR-E3/19K RD). The Universal T (UT) construct can hijack ERAD machinery to arrest TCR and HLA molecules in endoplasmic reticulum (ER) and facilitate their translocation into the cytoplasm for ubiquitination and degradation by proteasomes.

20 Claims, 8 Drawing Sheets

Specification includes a Sequence Listing.

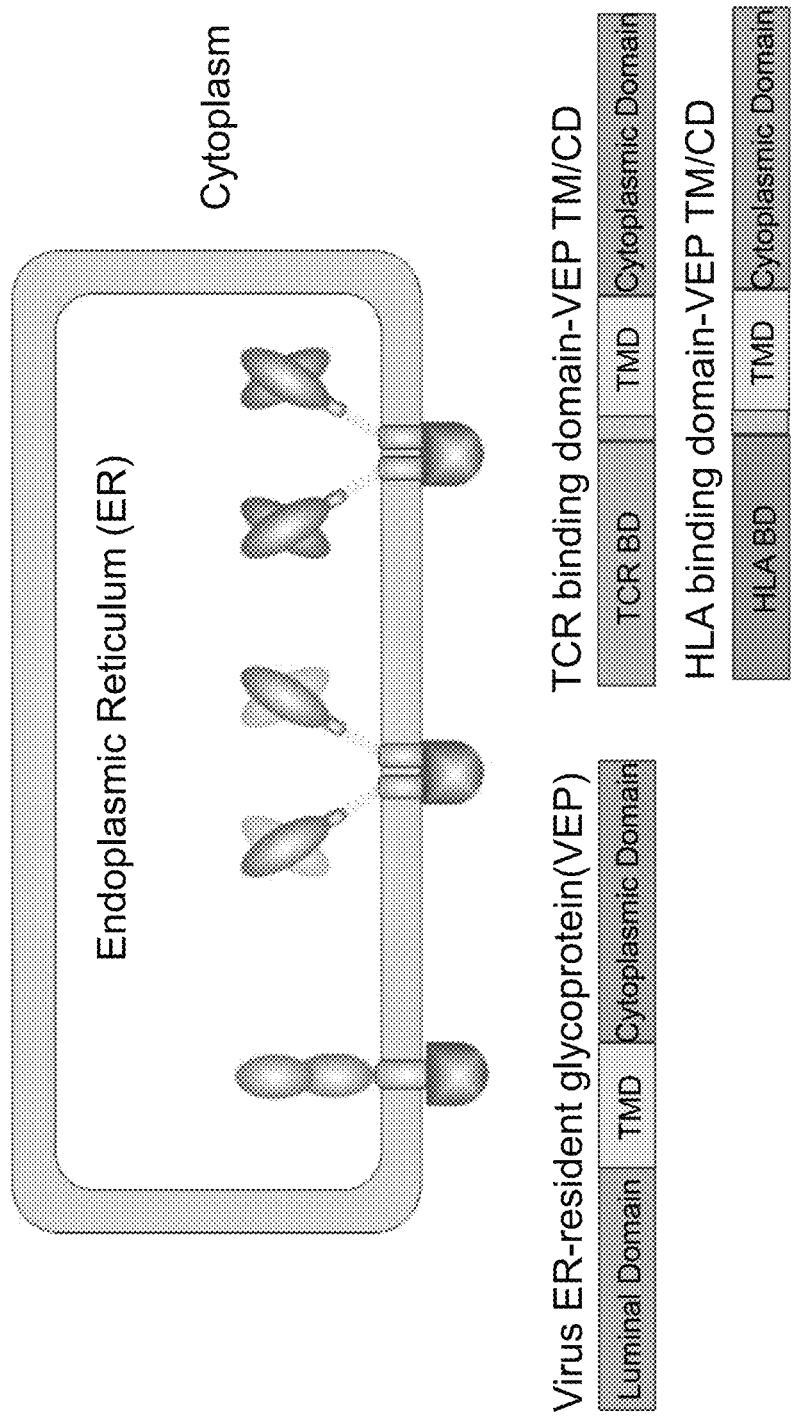
Fig. 1A. Schematic drawing and composition of UT chimeric multi-domains

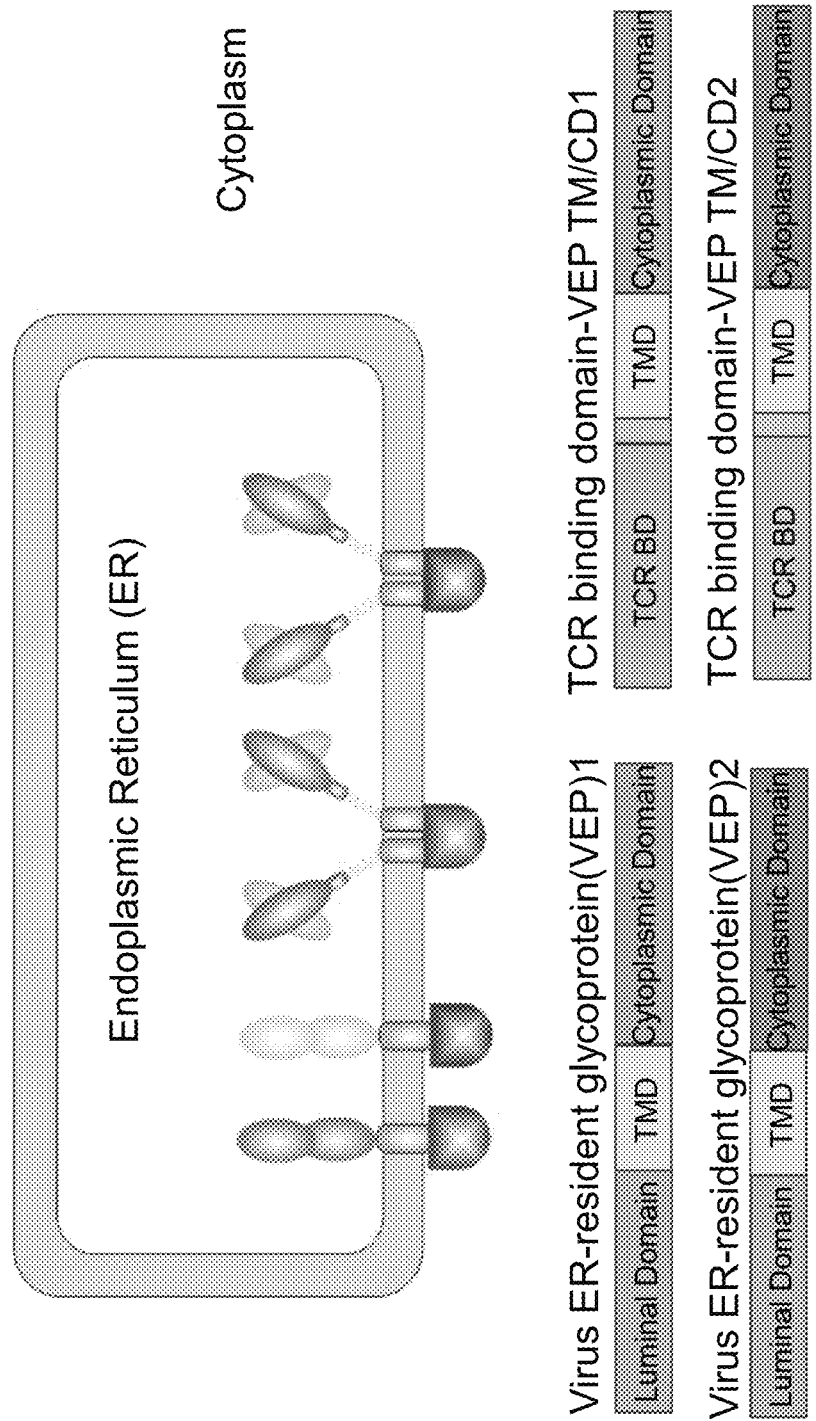
Fig. 1B. Schematic drawing and composition of UT chimeric multi-domains

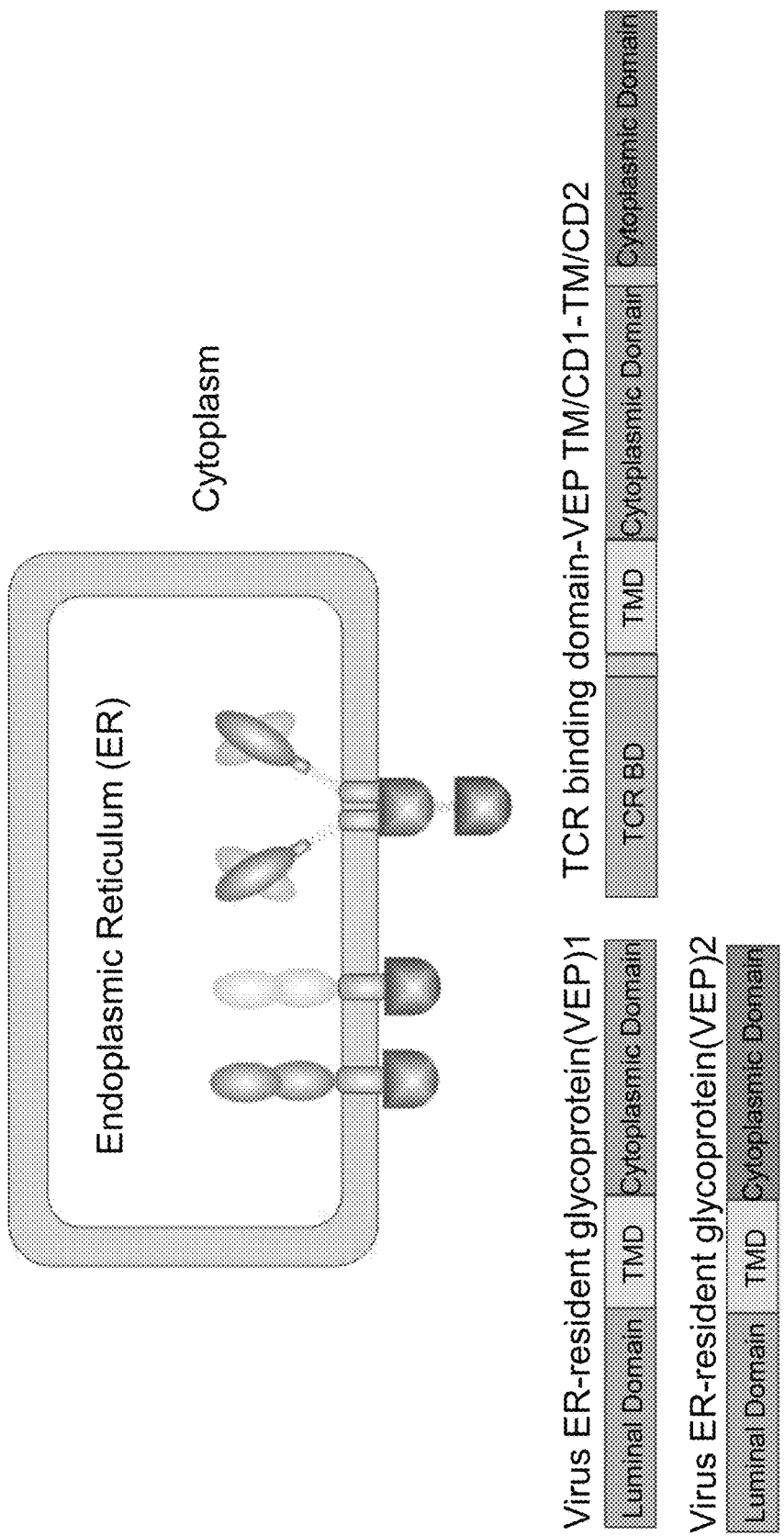
Fig.1C. Schematic drawing and composition of UT chimeric multi-domains

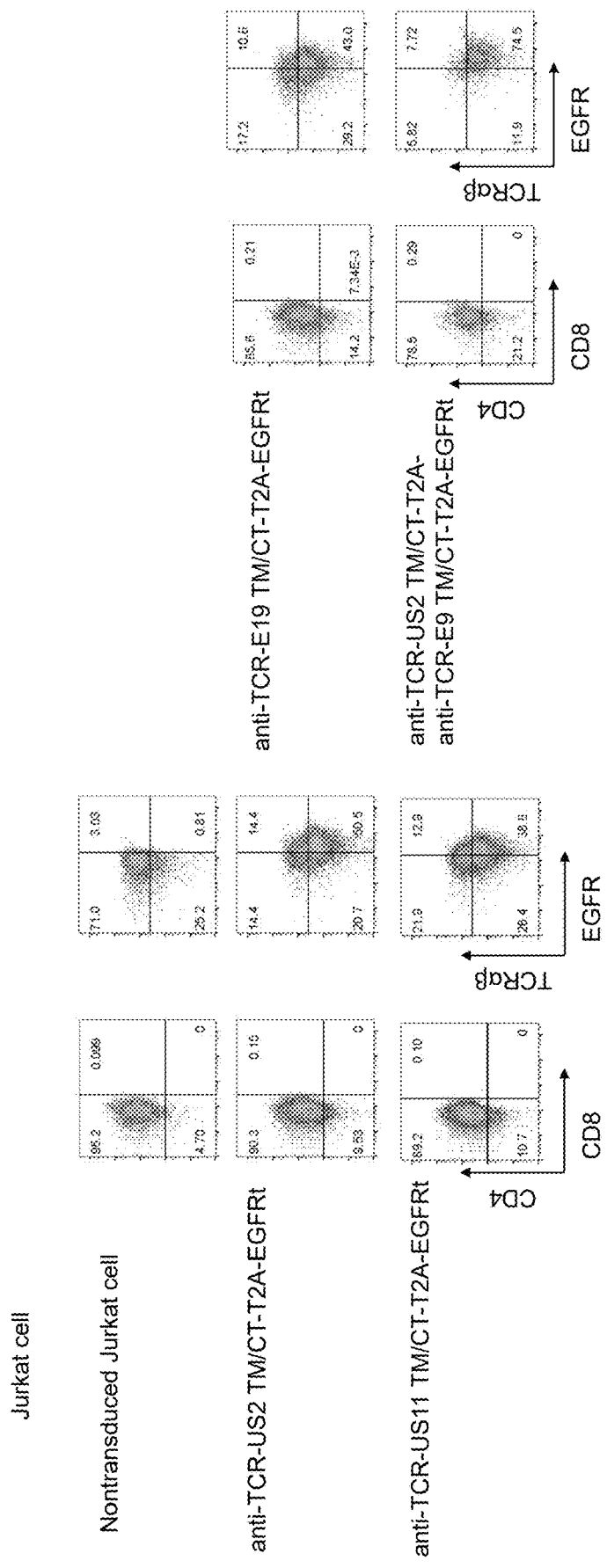
Fig. 2. Forced expression of UT elements could efficiently suppress TCR expression in Jurkat cells.

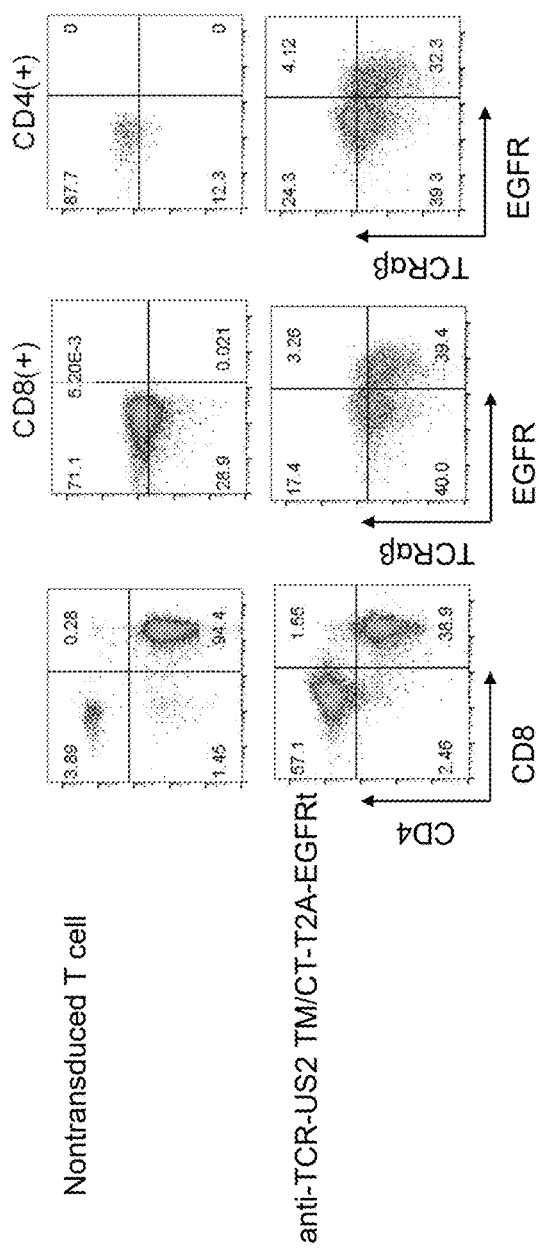
Fig. 3A. Forced expression of UT elements could efficiently suppress TCR expression in human T cells.

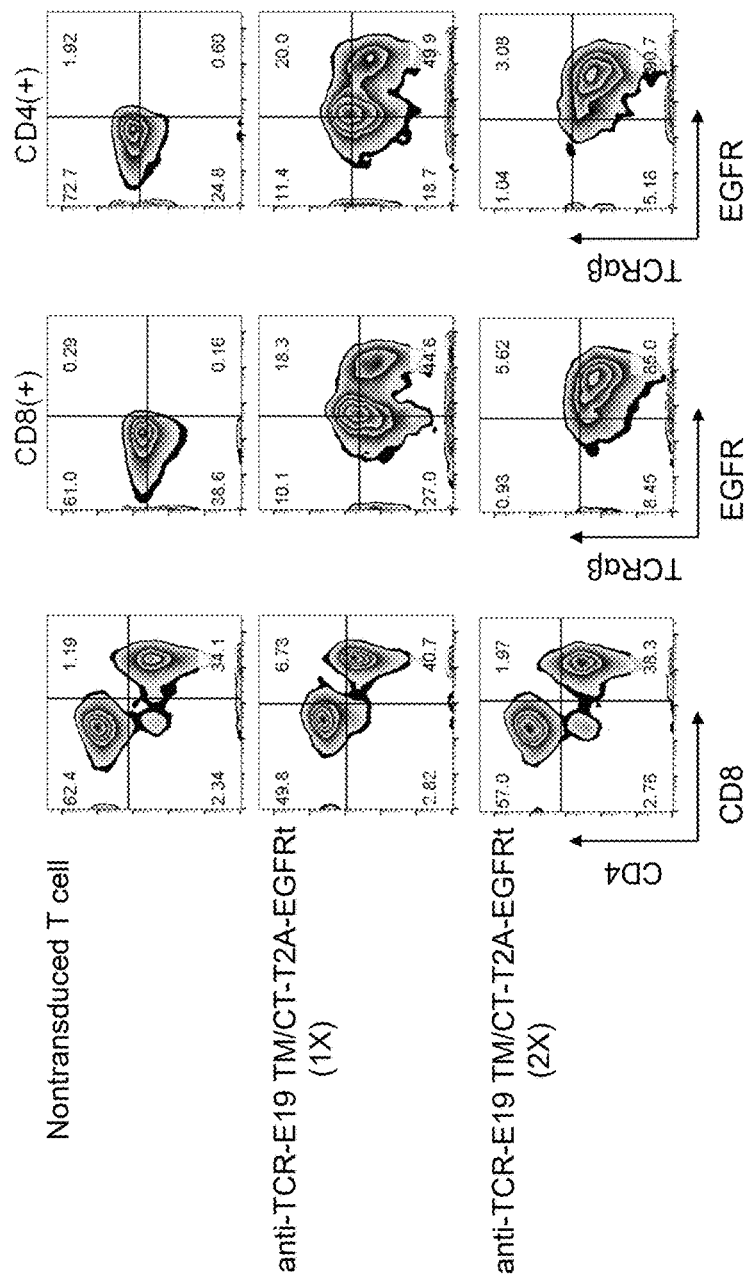
Fig. 3B. Forced expression of UT elements could efficiently suppress TCR expression in human T cells.

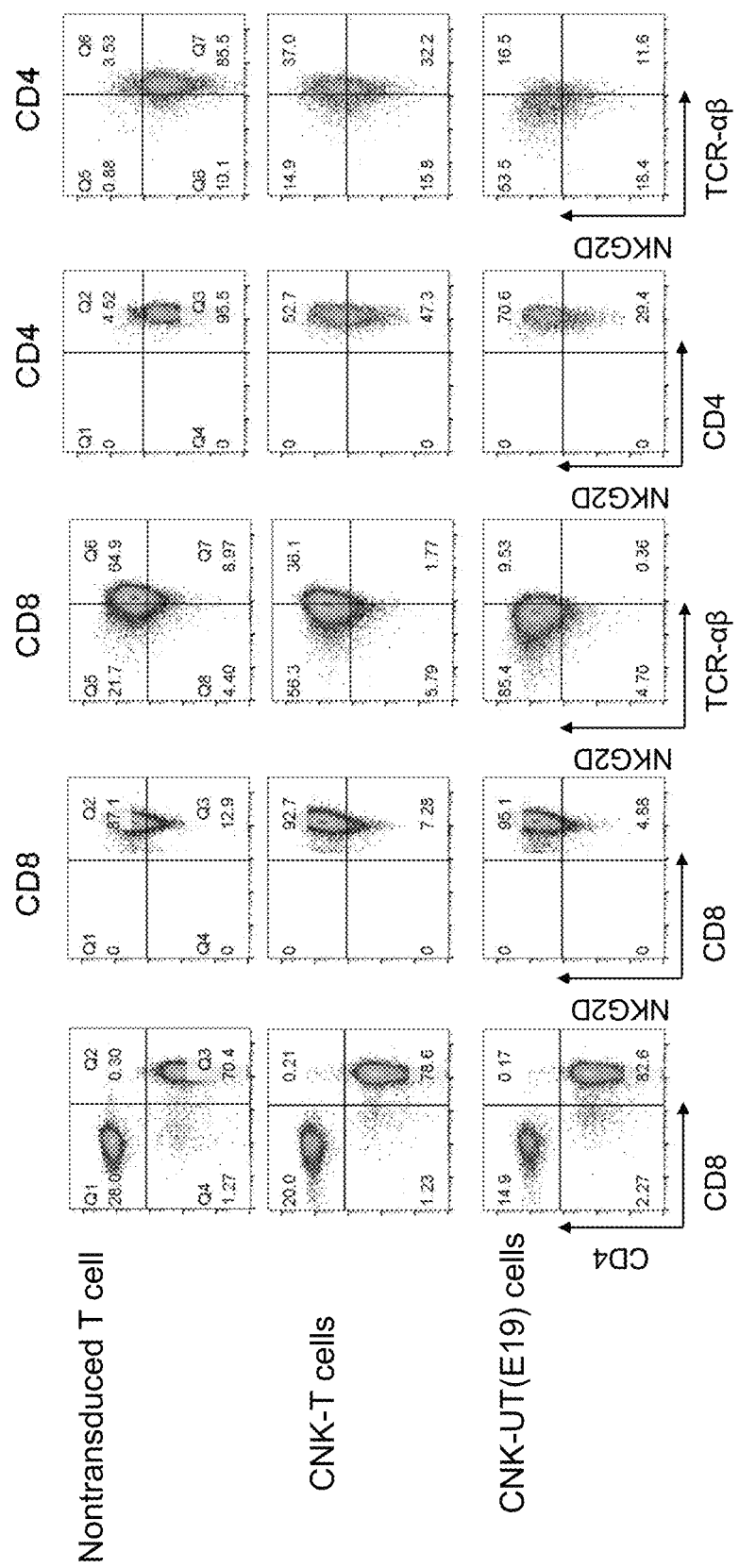
Fig. 4. CNK-T cell with UT elements downregulates TCR expression on both CD8/CD4 cells.

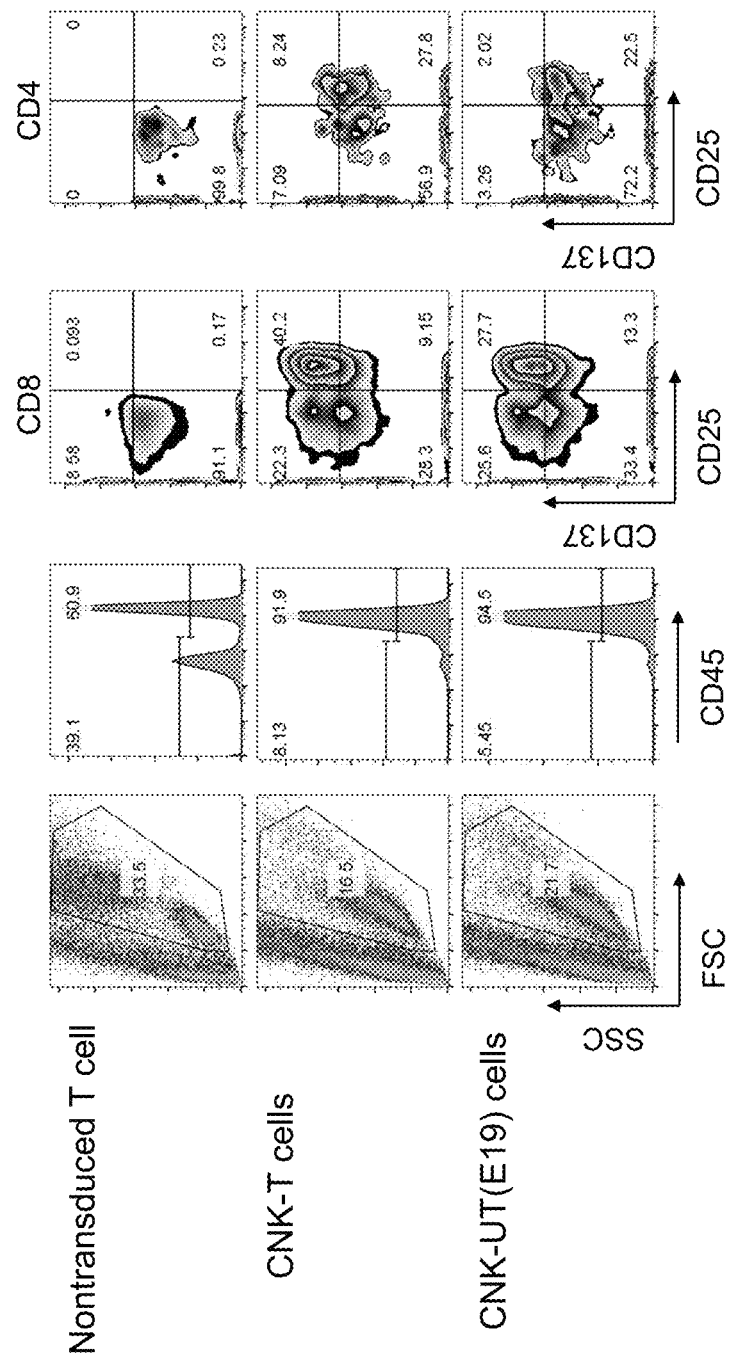
Fig. 5. CNK-T cell with UT elements display potent cytotoxicity against the tumor cells as the regular CNK-T cells.

UNIVERSAL T CELLS AND THE METHOD OF USE THEREOF

CROSS REFERENCE TO RELATED APPLICATION

This application claims the priority of provisional application 62/968,071, filed Jan. 30, 2020, titled "Design of Universal T Cells and the Method of Use Thereof," the content of which is hereby incorporated by reference in its entirety.

TECHNICAL FIELD

The present invention is related to immunological therapy in general; and in particular, provides novel compositions and methods to disrupt T cell receptor (TCR), human leukocyte antigens (HLA) class I and NKG2D (Natural-Killer Group 2, member D) ligand expression to generate highly compatible autologous universal T cells for further genetically engineering for allogeneic administration.

BACKGROUND OF INVENTION

The present invention provides novel compositions and methods to disrupt T cell receptor (TCR), human leukocyte antigens (HLA) class I and NKG2D (Natural-Killer Group 2, member D) ligand expression to generate highly compatible autologous universal T cells for further genetically engineering for allogeneic administration. The Universal T (UT) composition is comprised of TCR antibody fragment fused to transmembrane domain (TMD) and ER retention domain of adenovirus early region 3 glycoprotein E3-19k (E3/19K) (TCR-E3/19K RD) and full length of E3/19K.

The immune system has a near limitless capacity for detecting abnormalities. This remarkable ability for self-interrogation is achieved by the related structures of two molecules, immunoglobulins and T cell receptors (TCR). The TCR, a defining structure of T cells, is a transmembrane heterodimer consisting of either an alpha and beta chain or delta and gamma chain linked by a disulfide bond. Within these chains are complementary determining regions (CDRs) which determine the antigen to which the TCR will bind. In the TCR, the TCRα and TCRβ subunits (or TCRγ and TCRδ in γδ T cells) are responsible for the recognition of the Major histocompatibility complex (MHC)/antigen ligand.

Humans have three main MHC class I genes, known as HLA-A, HLA-B, and HLA-C. The proteins produced from these genes are present on the surface of almost all cells. On the cell surface, these proteins are bound to protein fragments (peptides) that have been exported from within the cell. MHC class I proteins display these peptides to the immune system. If the immune system recognizes the peptides as foreign (such as viral or bacterial peptides), it responds by triggering the infected cell to self-destruct.

Since the MHC class I molecule is a key factor in the modulation of the immune response against viral pathogens, the virus develops the strategies to target the class I molecules to avoid immune surveillance and clearance (Lybarger et al., 2005; Petersen et al., 2003; Tortorella et al., 2000). Evolving alongside its host for millions of years, the human cytomegalovirus (HCMV) has committed a large percentage of its genome toward modulation of the cellular response to infection (Mocarski., 2002) . . . . The HCMV unique short (US) genomic region encodes at least five glycoproteins (US2, US3, US6, US10, US11) that use specialized mechanisms for the down-regulation of MHC class I molecules, thereby hindering antigenic presentation to cytotoxic T lymphocytes (CTL).

CMV US glycoprotein is able to hijack the ER-associated degradation (ERAD) machinery to suppress MHC molecules mediated virus antigen presentation and thus escape the immune surveillance system. ER-associated degradation (ERAD) is a protein clearance system (Vembar and Brodsky, 2008).

Misfolded, misassembled, or metabolically regulated proteins in the ER are selectively dislocated from the ER into the cytosol via specific membrane penetration machinery and subsequently degraded by the cytosolic ubiquitin proteasome system (UPS) (Hershko and Ciechanover, 1998)

Both HCMV US2 and US11 are ER resident type I integral membrane glycoproteins, that co-opt this ERAD pathway to promote degradation of the MHC class I heavy chain and hence inhibit MHC class I antigen presentation. Expression of either protein causes rapid degradation of newly synthesized MHC class I heavy chains. US2 and US11 bind to the heavy chain via their luminal domains and recruit host cell proteins that extract the polypeptide from the ER membrane by 'pulling' on the cytosolic tail of the heavy chain. After translocation into the cytoplasm, the class I molecules is ubiquitinated and degraded by proteasomes (Eric W Hewitt., 2003).

Besides class I molecules, US2 also causes the degradation of two proteins of the class II pathway, DR-α and DM-α (Chevalier et al., 2002; Tomazin et al., 1999), as well as of HFE, a nonclassical major histocompatibility complex (MHC) class I protein involved in the regulation of iron (Ben-Arieh et al., 2001).

The luminal domain of US2 is responsible for binding of MHC class I and II molecules and transmembrane domain (TM) and cytoplasmic domain (CT) interacts with the cellular components of the ER-associated degradation pathway and contribute to translocation and forwarding both class I and II proteins for proteasomal degradation (Chevalier M S et al., 2002,2003). The cytosolic tail of US2 is sufficient for interaction with signal peptide peptidase (SPP), which is a necessary component of the US2-dependent MHC I dislocation complex (Loureiro J et al., 2006). In addition, US2 interacts with TRC8, the ER-resident RING-type E3-ligase, via its TM domain, which also contribute to the ubiquitination and proteasomal degradation of US2-tail-anchored MHC I and II molecule (Stagg H R et al., 2009).

By contrast, US11-induced degradation of MHC-I molecules requires Derlin1 but not SPP. The ER luminal domain of US11 interacts with the luminal domain of the MHC-I heavy chain, whereas the TM domain of US11 binds to Derlin-1. Thus, the major function of US11 is likely to be the delivery of MHC-I molecules to Derlin-1 (Lilley B N et al., 2004; Cho S et al., 2013), which then induces their dislocation to the cytosol for proteasomal degradation. In addition, US11 activates the unfold protein. Via Derlin-1, US11 Associates with TMEM129 which is an ERAD RING E3 Ligase and Recruits Ube2J2 to Ubiquitinate MHC-I Before US11-Induced Degradation (van den Boomen D J et al., 2014).

Instead promoting degradation of MHC protein, US3 glycoprotein binds physically to peptide-loaded MHC class I heterodimers which causes the retention of class I complexes in the ER and inhibits the association of invariant chains with class II DR-αβ dimers in the ER, causing the mislocalization of class II complexes and reduced peptide loading (Hegde N R et al., 2002). Therefore, US3 is able to interferes with the intracellular transport and maturation of MHC class I molecules during the immediate-early phase of HCMV infection (Ahn K et al., 1996; Jones T R et al., 1996). US3 is an ER-resident membrane protein, comprised of an ER-luminal domain bearing a single N-linked glycan at Asn 60, a single transmembrane domain and a short cytoplasmic tail (Ahn K et al., 1996). Domain swap experiments have shown that the luminal domain of US3 is sufficient for ER retention of US3 itself, whereas both luminal and transmembrane domains are required for retention of class I MHC molecules in the ER (Hegde N R et al., 2002).

In addition to MHC I molecules, US2 and US3 glycoprotein inhibit class II antigen presentation by destroying or abolishing the functions of class II proteins ((Chevalier M S et al., 2002; Chevalier M S et al, 2003, Tomazin R et al., 1999). US2 binds to class II DR and causes rapid and efficient proteosome-mediated degradation of only the α chain of the class II DR αβ complex. US2 also causes degradation of the α chain of DM, an MHC class II complex required for loading of antigenic peptides onto class II DR complexes. HCMV US3 binds to class II DR αβ heterodimers, inhibiting binding of the invariant chain (Ii), leading to intracellular mislocalization and reduced peptide loading of DR complexes (Hegde N R et al., 2002).

HCMV US10 encodes an ER membrane glycoprotein that also interacts with constituents of MHC class I antigen presentation. US10 binds free class I heavy chains and delays their transport from the ER. However, US10 does not influence US2 or US11 (Furman M H et al., 2002).

The adenovirus gene product E3/19K (E19) could also retain class I molecules in the secretary pathway and interfere with antigen presentation. E19 is also ER-resident glycoprotein which could abrogate cell surface transport of major histocompatibility complex class I (MHC-I) and MHC-I-related chain A and B (MICA/B) molecules. E3/19K comprises three functional modules: a luminal domain for interaction with MHC-I and MICA/B molecules, the transmembrane domain and a dilysine motif in the cytoplasmic tail that confers retrieval from the Golgi apparatus back to the ER. The studies suggested transmembrane domain (TMD) together with the ER retrieval signaling are required to ensure efficient ER localization, transport inhibition of MHC-I and MICA/B molecules and proteasomal degradation.

Unlike US2, US3, US10, and US11, the HCMV L protein US6 affects antigen presentation by an entirely different strategy. As opposed to interacting with free class I heavy chains or fully assembled class I complexes, US6 inhibits the translocation of cytosolic peptides by the TAP complex (TAP1/2) (Lehner P J et al., 1997). US6 binds to the ER luminal side of TAP1 and causes a conformational change that prevents the binding of ATP (Ahn K et al., 1997). Residues 89-108 in the ER-luminal domain of US6 contribute to binding of US6 to TAP and are sufficient and necessary for this inhibition (Dugan G E et al., 2008). This inhibition of TAP activity affects not only expression of classical MHC class I alleles but also the non-classical alleles HLA-C and HLA-G in fetal cytotrophoblasts (Jun Y et al., 2000)

As HCMV US6 protein, HSV ICP47, expressed very early in the infectious cycle that is dispensable for in vitro replication, could also apply the same strategy to block class I molecule assembly. ICP47 blocks TAP-mediated peptide transport and is tightly bound to the TAP1-TAP2 complex, (Früh et al 1995, Hill et al 1995). A clue to the mechanism of ICP47 blockade of TAP is that it exhibits a high species selectivity. Both HSV1 and HSV2 ICP47 inhibit ape, monkey, pig, dog, and cow TAP and have little effect on mouse, rat, guinea pig, or rabbit TAP (Jugovic et al 1998). The affinity of ICP47 to human TAP is approximately 100-fold higher than for mouse TAP (Ahn et al 1996b). ICP47 inhibits peptide binding to TAP, but does not affect ATP binding. With an affinity for TAP of 10-1000-fold greater than most peptides, ICP47 acts as a competitive inhibitor of peptide binding to TAP and is thought to bind directly to the peptide-binding site (Tomazin R et al., 1996; Ahn K et al., 1996).

Alpha/beta T lymphocytes recognize peptide-MHC ligands by means of a multimeric protein ensemble termed the αβ T cell antigen receptor (TCR). CD3 complex. This structure is composed of a variable αβ TCR dimer which binds antigens and three invariant dimers (CD3γε, δε and ζζ) which are involved in TCR. CD3 surface transport, stabilization and signal transduction. The alpha beta T cell receptor (αβTCR) is expressed on the majority (approx. 95%) of T cells and has a critical role in T cell activation via recognition of major histocompatibility complex (MHC)-anchored antigen. Therefore, TCR-mediated activation of T cells is the key step of the pathogenesis of graft versus host disease (GVHD) during the Allogeneic hematopoietic cell transplantation (allo-HCT) and allogeneic CAR-T cell therapy.

The human leukocyte antigen (HLA) system or complex is a group of related proteins that are encoded by the major histocompatibility complex (MHC) gene complex in humans. These cell-surface proteins are responsible for the regulation of the immune system. In therapeutic transplant setting, "HLA mismatch" happens when the donor HLA on the allograft differs from the recipient. HLA mismatch leads to the activation of alloreactive T cells, which can cause acute cellular rejection (ACR) within six months of transplantation. Mismatched donor HLA antigens are also targets for the development of de nova donor-specific HLA antibodies (dnDSA) which play augmented roles in both acute and chronic transplant T cell rejection.

Therefore, to generate universal T cells for safe allogenic infusion and therapeutic purpose, it is advisable to effectively block graft-versus-host disease (GVHD) by genetically disrupting the TCR. In addition, it is necessary to suppress HLA expression on the allogeneic T cell to reduce rejection of the recipient immune system. on allogeneic T cell TCRαβ and/or HLA class I of the allogeneic T cells.

Herein, we disclose a novel composition of Universal T (UT) elements which could hijack ERAD machinery to arrest TCR, HLA molecules in ER, block its transportation and facilitate its translocation into the cytoplasm for ubiquitination and degradation by proteasomes.

In addition, such design could target any endogenous protein for efficient inhibition of expression and fast degradation for therapeutic purpose.

SUMMARY OF INVENTION

The present invention is based on the discovery that virus ER-resident glycoprotein could hijack ERAD tuning machinery to inhibit/block MHC molecules assembly, transportation and promote its ubiquitination and degradation by proteasome, thus suppress viral antigen presentation and enable immune escape. Accordingly, the present invention provides a hybrid multi-domain construct or a composition that targets TCR or HLA molecules for post-translational expression suppression and degradation to generate universal T cell for allogeneic transfusion of therapeutic purpose. The present invention also provides a composition to target other proteins and the use thereof.

In one embodiment, the present invention provides a hybrid multi-domain construct or composition of UT elements and methods to generate highly compatible autologous universal T cells for further genetically engineering for allogeneic administration for therapeutic use. The composition comprises a αβTCR or HLA affinity molecules fused to transmembrane domain (TMD) and ER retention domain of the virus ER-resident glycoprotein.

In one embodiment, a TCRαβ or HLA affinity molecules is antibody fragment that specific recognizes and binds to the constant region of αβTCR or HLA. In one embodiment, the virus ER-resident glycoprotein could be any viral ER-resident protein which is capable of hijacking ERAD machinery to arrest MHC molecules in ER and promoting its ubiquitination and degradation by proteasome. In certain embodiments, the ER-resident protein could be HCMV glycoprotein US2, US3, US11 and US10, adenovirus E19.

In one embodiment, the virus ER-resident glycoprotein could be any viral protein which is capable of blocking TAP-mediated Peptide transport into the ER and inhibit MHC molecules assembly. In certain embodiments, the ER-resident protein could be HCMV glycoprotein US6, HSV ICP47.

In one embodiment, the composition comprises one or more the full-length viral protein, which could directly block MHC molecules assembly, such as US2, US3, US6, US11 and US10, adenovirus E19, HSV ICP47 et al.

In certain embodiment, the lentiviral vector or retroviral vector encoding the anti-human TCR or HLA alpha/beta scFv fused to E19 transmembrane domain (TM) and cytoplasmic domain (CT) and full length E19 sequence can be used to transduce human T cells alone or with the gene sequence encoding the other functional receptors/molecules, such as chimeric antigen receptor (CAR) or chimeric NK receptor et al to further genetically engineer T cells to become the therapeutic products to treat cancer and other diseases.

In certain preferred embodiments, the lentiviral vector or retroviral vector encoding the TCR-E19 TM/CT domain and E19 sequence can be used to transduce human T cells alone or with the gene sequence encoding the other functional receptors/molecules, such as chimeric antigen receptor (CAR), chimeric NK receptor, cytokine, chemokine et al. After expansion in vitro, the genetically engineered allogeneic T cells can be negatively selected based on TCR expression and safely transfused into the patients to treat various diseases, such as cancer, virus-infected disease, autoimmune diseases et al.

The Universal T (UT) composition is comprised of TCR or HLA antibody fragment fused to transmembrane domain (TMD) and ER retention domain of the virus ER-resident glycoprotein, such as US2, US3, US6, US11, E19, ICP47 and full length of such glycoprotein which could efficiently target both TCR and HLA to generate highly compatible autologous universal T cells for further genetically engineering for allogeneic administration.

BRIEF DESCRIPTION OF THE DRAWINGS

FIG. 1A is a schematic drawing and composition of UT chimeric multi-domains. The wide-type structure of one virus ER-resident glycoprotein (VEP), which is composed of luminal domain (LD), transmembrane domain (TMD) and cytoplasmic functional domain; UT chimeric multi-domain is composed of TCR or HLA binding domain, hinge/spacer, VEP transmembrane and cytoplasmic domain.

FIG. 1B is a schematic drawing and composition of UT chimeric multi-domains. The wide-type structure of different virus ER-resident glycoproteins (VEP), which is composed of different luminal domain (LD), transmembrane domain (TMD) and cytoplasmic functional domain; UT chimeric multi-domain is composed of TCR or HLA binding domain, hinge/spacer, with different VEP transmembrane and cytoplasmic domain;

FIG. 1C is a schematic drawing and composition of UT chimeric multi-domains. The wide-type structure of different virus ER-resident glycoproteins (VEP), which is composed of different luminal domain (LD), transmembrane domain (TMD) and cytoplasmic functional domain; UT chimeric multi-domain is composed of TCR or HLA binding domain, hinge/spacer, with the different VEP transmembrane and chimeric cytoplasmic domains derived from different VEP.

FIG. 2 shows forced expression of UT elements could efficiently suppress TCR expression in Jurkat cells; The lentiviral vector with truncated EGFR is encoding anti-TCR scFv fused to different viral ER-resident protein, HCMV US2, US3, US11, Adenovirus E19 TM/CT domain, and the lentiviral vector encoding both anti-TCR scFv fused to both US2 and adenovirus E19 TM/CT were constructed. The Jurkat cells were transduced with such lentivirus and non-transduced Jurkat cells were used as control. 48 h post-transduction, the cells were submitted to flow cytometry to detect TCRαβ expression in the transduced cells (EGFR+ cells). The result shows that all EGFR (+) Jurkat displays significant downregulation of TCRαβ expression; the cells transduced with combined UT composition (US2/E19) could efficiently block TCRαβ expression. All the tested UT chimeric elements (US2, US3, US11, E19) could block TCRαβ expression. Combine UT elements (US2 and E19) could significantly improve the suppression of TCRαβ expression on the Jurkat cell surface.

FIG. 3A shows forced expression of UT elements could efficiently suppress TCR expression in human T cells. The lentiviral vector with expression cassette including truncated EGFR is encoding anti-TCR scFv fused to HCMV US3 TM/CT domain (anti-TCR-US2 TM/CT-T2A-EGFRt). The human T cells were stimulated and transduced with such lentivirus and the nontransduced T cells as control. 5 days after transduction, the cells were submitted to flow cytometry to detect TCRαβ expression in the transduced T cells (EGFR+ cells). The result shows that EGFR (+) T displays significant downregulation of TCRαβ expression compared to the nontransduced T cells. It indicates US elements containing anti-TCR-US3 TM/CT could efficiently suppress TCRαβ expression in human T cells.

FIG. 3B shows forced expression of UT elements could efficiently suppress TCR expression in human T cells. The lentiviral vector with expression cassette including truncated EGFR is encoding anti-TCR scFv fused to HCMV E19 TM/CT domain (anti-TCR-E19 TM/CT-T2A-EGFRt). The human T cells were stimulated and transduced with such lentivirus and the nontransduced T cells as control. 5 days after transduction, the cells were submitted to flow cytometry to detect TCRαβ expression in the transduced T cells (EGFR+ cells). The result shows that EGFR (+) T displays significant downregulation of TCRαβ expression compared to the nontransduced T cells. Increased virus transduction could further improve the suppression of TCRαβ expression on the T cell surface. It indicates US elements containing anti-TCR-E19 TM/CT could efficiently TCRαβ expression in human T cells.

FIG. 4 shows CNK-T cell with UT elements downregulates TCR expression on both CD8/CD4 cells;

The lentiviral vector contains the expression cassette encoding chimeric NK receptor and anti-TCR scFv fused to E19 TM/CT domain (CNK-UT-E19). The human T cells were transduced with such lentivirus. 5 days post-transduction, the cells were submitted to flow cytometry to detect TCRαβ expression in the transduced cells (NKG2D+ cells), the regular chimeric NK receptor transduced T cells and nontransduced T cells as control. The results show introduction of UT elements into CNK expression cassette will not affect chimeric NK receptor expression. Moreover, it could significantly suppress TCR expression on both CD8+ and CD4+ CNK-T cells.

FIG. 5 shows CNK-T cell with UT elements display potent cytotoxicity against the tumor cells as the regular CNK-T cells.

Non-transduced T cells, CNK-T cells and CNK-UT (E19) cells were co-culture with HepG2 cells at E:T ratio=1:5. 24 h post-culture, the cells were harvested and submitted to flow analysis for detect the tumor lysis and T cell activation. The data indicates the CNK-UT cells display comparable potent cytotoxicity against HepG2 cells as regular CNK-T cells. After 24 h co-culture, the CD45 (−) tumor cells were significantly decreased in the co-culture with CNK-T as well as CNK-UT. In addition, both CD8 and CD4 CNK-UT cells can upregulate CD25 and CD137 after co-culture with HepG2 cells.

DETAILED DESCRIPTION OF THE PREFERRED EMBODIMENTS

The following examples of the invention are included by way of illustration, and not by way of limitation.

The concept of UT composition is based on the the discovery that virus ER-resident glycoprotein could hijack ERAD tuning machinery to inhibit/block MHC molecules assembly, transportation or promote its ubiquitination and degradation by proteasome, thus suppress MHC-mediated viral antigen presentation for escape of immune surveillance. Efficient downregulation of TCR will significantly suppress the TCR-mediated immune attack and reduce GVHD during allogeneic transfusion of T cells. Including the natural viral ER-resident glycoprotein could further suppress MHC molecules and thereby preventing peptide presentation to recipient CD8+ T cells and suppress immune recognition of allogeneic T cells. Therefore, the UT composition can improve the compatibility and long-term persistence of allogeneic T cells after infusion. For cellular therapeutic purpose, the universal T cells with defective surface expression of TCRαβ and MHC molecules could be further genetically engineered for therapeutic purpose.

Embodiment 1

UT Elements and Derivatives Thereof

Exemplary chimeric fusion proteins containing TCRαβ or HLA molecules binding moiety, one or more transmembrane and cytoplasmic domains of viral ER-resident protein in cassettes are illustrated in FIG. 1. For example, in FIG. 1A, the chimeric fusion proteins include the anti-TORαβ or HLA antibody fragment scFv, Hinge/linker (e.g. SEQ NO. 5. IgG4 hinge; and SEQ ID NO. 15 (Gly 4 Ser)2 and fused to any transmembrane domain and cytoplasmic domain of ER-resident glycoprotein, e.g. HCMV US2 (SEQ ID NO. 19 and NO. 20). For example, in FIG. 1B, the chimeric fusion proteins include the anti-TCRαβ or HLA antibody fragment scFv, Hinge/linker (e.g. SEQ NO. 5. IgG4 hinge; and SEQ ID NO. 15 (Gly 4 Ser)2 and fused to two or more transmembrane domain and cytoplasmic domain of ER-resident glycoprotein, e.g. HCMV US2 (SEQ ID NO. 19 and NO. 20) and HCMV US3 (SEQ ID NO. 20 and NO. 21). For example, in FIG. 1C, the chimeric fusion proteins include the anti-TORαβ or HLA antibody fragment scFv, Hinge/linker (e.g. SEQ NO. 5. IgG4 hinge; and SEQ ID NO. 15 (Gly 4 Ser)2 and fused to the recombinant motif of transmembrane domain and cytoplasmic domain derived from various ER-resident glycoprotein, e.g. HCMV US2 (SEQ ID NO. 19 and NO. 20) and HCMV US11 (SEQ ID NO. 19, NO. 20, NO. 22, NO. 23).

This UT elements encoding nucleic acid molecule was cloned into the lentiviral vector and then transduced into Jurkat cells or human T cells.

Embodiment 2

Transduced UT Elements Efficiently Block TCRαβ Expression in Jurkat Cells.

An exemplary lentiviral construct encoding the UT element comprising anti-TCRαβ fused to the transmembrane and cytoplasmic domain of HCMV US2 or HCMV US11 or/and adenovirus E19, T2A self-cleavage peptide, truncated EGFR was designed (named anti-TCR-US2 TM/CT-T2A-EGFRt; anti-TCR-US11 TM/CT-T2A-EGFRt; anti-TCR-E19 TM/CT-T2A-EGFRt; anti-TCR-US2-TM/CT-T2A-anti-TCR-E19 TM/CT-T2A-EGFRt). The DNA was synthesized and cloned into the lentiviral vector (such as pLenti CMV GFP-puro) and lentivirus were produced in 293T cells, using the package vectors (such as psPAX and pMD2G). Jurkat cells were culture in RPMI, 10% human serum, 2 mM L-glutamine and 1% penicillin-streptomycin (CTL medium) and then transduced with a lentiviral supernatant (as indicated) (MOI=3) supplemented with 0.8 µg/mL polybrene (Millipore, Bedford, MA). After 3 days expansion, the cells were submitted to flow cytometry to examine expression of truncated EGFR and TCRαβ in Jurkat cells (FIG. 1). The following conjugated antibodies were used for flow cytometric phenotypingvand analysis: CD4-APC, CD8-Pacific Blue, TCR-ab-APC-Cy7, EGFR-PE (Biolegend). Staining with propidium iodide (PI, BD Biosciences) was performed for live/dead cell discrimination as directed by the manufacturer. Flow analyses were done on a FACS Canto II, sort-purifications on a FACS Ariall (Becton Dickinson, Franklin Lakes, NJ) and data analyzed using FlowJo software (Treestar, Ashland, OR) The result indicated the transduced cells expressed the truncated EGFR and significant downregulation of on TCRαβ on both CD8+ and CD4+ T cells, while the nontransduced Jurkat cells express high level of TCRαβ in absence of truncated EGFR.

Embodiment 3

Forced Expression of UT Elements could Efficiently Suppress TCR Expression in Human T Cells.

In FIG. 3A, an exemplary lentiviral construct encolding the UT element comprising anti-TCRαβ fused to the transmembrane and cytoplasmic domain of HCMV US2, T2A self-cleavage peptide and truncated EGFR was designed (named anti-TCR-US2 TM/CT-T2A-EGFRt were cloned into the lentiviral vector (such as pLenti CMV GFP-puro) and lentivirus were produced in 293T cells, using the package vectors (such as psPAX and pMD2G). Human CD8+ and CD4+ were isolated from PBMC of normal donors using CD3+ T Cell Isolation Kit (Miltenyi Biotec), activated with anti-CD3/CD28 beads (Life Technologies) according to the manufacturer's instructions, and transduced with a lentiviral supernatant (as indicated in each Example) (MOI=3) supplemented with 0.8 μg/mL polybrene (Millipore, Bedford, MA) on day 3 after activation by centrifugation at 2,100 rpm for 45 min at 32° C. T cells were expanded in RPMI, 10% human serum, 2 mM L-glutamine and 1% penicillin-streptomycin (CTL medium), supplemented with recombinant human (rh) IL-2 to a final concentration of 50 U/mL every 48 hours. After 12 days expansion, an aliquot of each transduced T cell line was stained with CD8-Pacific Blue, CD4-APC, TCR-ab-APC-Cy7, EGFR-PE (Biolegend) and then submitted to flow cytometry analysis.

The result indicates that the transduced T cells (EGFR+) significantly downregulate TCRαβ expression on both CD8+ and CD4+ cell surface compared to the nontransduced T cells. In conclusion, US elements containing anti-TCR-US2 TM/CT could efficiently suppress TCRαβ expression in human T cells which may inhibit TCR-mediated GVHD in vivo after transfusion into different recipient.

In FIG. 3B, an exemplary lentiviral construct encolding the UT element comprising anti-TCRαβ fused to the transmembrane and cytoplasmic domain of adenovirus E19, T2A self-cleavage peptide and truncated EGFR was designed (named anti-TCR-E19 TM/CT-T2A-EGFRt were cloned into the lentiviral vector (such as pLenti CMV GFP-puro) and lentivirus were produced in 293T cells. Human CD8+ and CD4+ were transduced with two dose of lentiviral supernatant (1×, 2×) and expanded in CTL medium, supplemented with recombinant human (rh) IL-2. After 12 days expansion, an aliquot of each transduced T cell line was stained with CD8-Pacific Blue, CD4-APC, TCR-ab-APC-Cy7, EGFR-PE (Biolegend) and then submitted to flow cytometry analysis.

The result indicates that the UT (E19) transduced T cells (EGFR+) could also efficiently block TCRαβ expression on both CD8+ and CD4+ cell surface compared to the non-transduced T cells. Increase virus dose of transduction, the suppression of TCRαβ expression could be significantly improved with the increased transduction efficiency and copy number of UT elements in cells. In conclusion, US elements containing anti-TCR-E19 TM/CT could efficiently suppress TCRαβ expression in human T cells which may also inhibit TCR-mediated GVHD in vivo after transfusion into different recipient.

Embodiment 4

Phenotype of CNK-T Cells Expressing U-T Elements

In FIG. 4, an exemplary lentiviral construct encoding the CNK sequence, T2A sequence and UT element comprising anti-TCRαβ fused to the TM and CT domain of adenovirus E19, T2A self-cleavage peptide was designed (named CNK-UT-E19 were cloned into the lentiviral vector (such as pLenti CMV GFP-puro) and lentivirus were produced in 293T cells. Human CD8+ and CD4+ were transduced with two dose of lentiviral supernatant and expanded in CTL medium, supplemented with IL-2. After 12 days expansion, an aliquot of each transduced T cell line was stained with CD8-Pacific Blue, CD4-APC, TCR-ab-APC-Cy7, NKG2D-PE-Cy7 (Biolegend) and then submitted to flow cytometry analysis. The results indicate inclusion of UT elements in CNK-T cells could significantly suppress TCRαβ expression in CNK-T cells without interfere with the expression of NKG2D in both CD8+ and CD4+ T cells.

Embodiment 5

Cytotoxicity of CNK-T Cells Expressing U-T Elements

The in vitro effector function of CD3+ bulk T cells engineered to express CNK, or CNK-UT were compared to nontransduced T cells respectively—in the co-culture assay with the HCC cell line, HepG2 cells. Briefly, 0.5×10^6 HepG2 cells were seeded on 24 well plates 24 h before the co-culture. The HepG2 cells were added with 1×10^5 effector cells (E:T=1:5) and incubated in the 37 degree for another 24 h before analysis. After co-culture, the cells were harvested and stained with CD8-Pacific Blue, CD4-APC, CD45-PerCP-Cy5.5, CD25-APC-Cy7 and CD137-PE-Cy7 (Biolegend) and then submitted to flow cytometry analysis. The results indicates both CNK-T and CNK-UT (E19) could efficiently eliminate HepG2 in the co-culture assay compared to non-transduced T cells. In addition, CNK-UT cells significantly upregulate CD25 and CD137, the T cell activation markers, as regular CNK-T. In conclusion, inclusion of UT elements will not interfere T cell function, such as cytotoxicity against tumor cells.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments. These and other changes can be made to the embodiments in light of the above detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

```
(SEQ ID NO. 1) = IgG1 hinge:
EPKSCDKTHTCPPCP (SEQ ID NO. 2) = IgG2 hinge:
ERKCCVECPPCP (SEQ ID NO. 3) = IgG3 hinge:
LKTPLGDTTHTCPRCPEPKSCDTPPPCPRCPEPKSCDTPPPCPRCPEPK
SCDTPPPCPRCP (SEQ ID NO. 4) = IgG4 hinge:
ESKYGPPCPSCP (SEQ ID NO. 5) = lgG4 hinge(mutated):
ESKYGPPCPPCP (SEQ ID NO. 6) = IgA hinge:
PVPSTPPTPSPSTPPTPSPSC (SEQ ID NO. 7) = IgD hinge:
ESPKAQASSVPTAQPQAEGSLAKATTAPATTRNTGRGGEEKKKEKEKEE
QEERETKTP
```

-continued
(SEQ ID NO. 8) = IgM common heavy (CH):
IAELPPKVSVFVPPRDGFFGNPRKSKLICQATGFSPRQIQVSWLREGKQ
VGSGVTTDQVQAEAKESGPTTYKVTSTLTIKESDWLGQSMFTCRVDHRG
LTFQQNASSMCVPD (SEQ ID NO. 9) = IgE CH2:
PTVKILQSSCDGGGHFPPTIQLLCLVSGYTPGTINITWLEDGQVMDVDL
STASTTQEGELASTQSELTL SQKHWLSDRTYTCQVTYQGHTFEDSTKK
CA (SEQ ID NO. 10) = CD8a Hinge:
AKPTTTPAPRPPTPAPTIASQPLSLRPEACRPAA GGAVHTRGLDFACD (SEQ ID NO. 11) = CD8a Hinge:
TTTPAPRPPTPAPTIASQPLSLRPEACRPAAGGAVHTRGLDFACD (SEQ ID NO. 12) = CD8b Hinge:
SVVDFLPTTAQPTKKSTLKKRVCRLPRPETQKGPLCSP (SEQ ID NO. 13) = CD8b Hinge:
VDFLPTTAQPTKKSTLKKRVCRLPRP ETQKGPLCSP (SEQ ID NO. 14) = CD4 Hinge:
DSGQVLLESNIKVLPTWSTPVQP (SEQ ID NO. 15) = (Gly 4 Ser):
GGGGS (SEQ ID NO. 16) = (Gly 4 Ser)2:
GGGGSGGGGS (SEQ ID NO. 17) = (Gly 3Ser)2:
GGGSGGGS (SEQ ID NO. 18) = HCMV US2 TMD:
VAWTIVFYSINITLLVLFIVY (SEQ ID NO. 19) = HCMV US2 CD:
VTVDCNLSMMWMRFFVC (SEQ ID NO. 20) = HCMV US3 TMD:
TLLVYLFSLVVLVLLTVGVSA (SEQ ID NO. 21) = HCMV US3 CD:
RLRFI (SEQ ID NO. 22) = HCMV US11 TMD:
YTLMMVAVIQVFWGLYVKGWL (SEQ ID NO. 23) = HCMV US11 CD:
HRHFPWMFSDQW (SEQ ID NO. 24) = HCMV US10 TMD:
LGDYGAILKIYFGLFCGACVI (SEQ ID NO. 25) = HCMV US10 CD:
TRSLLLICGYYPPRE (SEQ ID NO. 26) = HCMV US6 TMD:
FFAVTLYLCCGITLLVVILAL (SEQ ID NO. 27) = HCMV US6 CD:
LCSITYESTGRGIRRCGS (SEQ ID NO. 28) = AV E19 TMD:
TFCSTALLITALALVCTLLYL (SEQ ID NO. 29) = AV E19 CD:
KYKSRRSFIDEKKMP (SEQ ID NO. 30) = HIV1 Vpu: TMD:
AIVALVVAIIIAIVVWSIVII (SEQ ID NO. 31) = HIV1 CD:
EYRKILRQRKIDRLIDRLIERAEDSGNESEGEISALVEMGVEMGHHAPW
DVDDL -continued
(SEQ ID NO. 32) = T2A:
(GSG)EGRGSLLTCGDVEENPGP (SEQ ID NO. 33) = P2A:
(GSG)ATNFSLLKQAGDVEENPGP (SEQ ID NO. 34) = E2A:
(GSG)QCTNYALLKLAGDVESNPGP (SEQ ID NO. 35) = F2A:
(GSG)VKQTLNFDLLKLAGDVESNPGP The contents of the following references are incorporated into the disclosure.

Chevalier, M. S., G. M. Daniels, and D. C. Johnson. 2002. Binding of human cytomegalovirus US2 to major histocompatibility complex class I and II proteins is not sufficient for their degradation. J. Virol. 76:8265-8275.

Tomazin, R., J. Boname, N. R. Hegde, D. M. Lewinsohn, Y. Altschuler, T. R. Jones, P. Cresswell, J. A. Nelson, S. R. Riddell, and D. C. Johnson. 1999. Cytomegalovirus US2 destroys two components of the MHC class II pathway, preventing recognition by CD4+ T cells. Nat. Med. 5:1039-1043.

Ben-Arieh, S. V., B. Zimerman, N. I. Smorodinsky, M. Yaacubovicz, C. Schechter, I. Bacik, J. Gibbs, J. R. Bennink, J. W. Yewdell, J. E. Coligan, H. Firat, F. Lemonnier, and R. Ehrlich. 2001. Human cytomegalovirus protein US2 interferes with the expression of human HFE, a nonclassical class I major histocompatibility complex molecule that regulates iron homeostasis. J. Virol. 75:10557-10562.

Ahn K, Meyer T H, Uebel S, Sempé P, Djaballah H. et al. Molecular mechanism and species specificity of TAP inhibition by herpes simplex virus protein ICP47. EMBO J. 1996b; 15:3247-55.

York I A, Roop C, Andrew D W, Riddell S R, Graham F L, Johnson D C. A cytosolic herpes simplex virus protein inhibits antigen presentation to CD8+T lymphocytes. Cell. 1994; 77:525-35.

Früh K, Ahn K, Djaballah H, Sempé P, van Endert P M. et al. A viral inhibitor of peptide transporters for antigen presentation. Nature. 1995; 375:415-18

Hill A, Jugovic P, York I, Russ G, Bennink J. et al. Herpes simplex virus turns off the TAP to evade host immunity. Nature. 1995; 375:411-14.

Furman M H, Dey N, Tortorella D, Ploegh H L. The human cytomegalovirus US10 gene product delays trafficking of major histocompatibility complex class I molecules. J Virol. 2002; 76 (22): 11753-6.

Hegde N R, Tomazin R A, Wisner T W, Dunn C, Boname J M, Lewinsohn D M, Johnson D C. Inhibition of HLA-DR assembly, transport, and loading by human cytomegalovirus glycoprotein US3: a novel mechanism for evading major histocompatibility complex class II antigen presentation. J Virol. 2002 November; 76 (21): 10929-41.

Chevalier M S, Daniels G M, Johnson D C. Binding of human cytomegalovirus US2 to major histocompatibility complex class I and II proteins is not sufficient for their degradation. J Virol. 2002 August; 76 (16): 8265-75.

Chevalier M S, Johnson D C. Human cytomegalovirus US3 chimeras containing US2 cytosolic residues acquire major histocompatibility class I and II protein degradation properties. J Virol. 2003 April; 77 (8): 4731-8.

Tomazin R, Boname J, Hegde N R, Lewinsohn D M, Altschuler Y, Jones T R, Cresswell P, Nelson J A, Riddell S R, Johnson D C. Cytomegalovirus US2 destroys two components of the MHC class II pathway, preventing recognition by CD4+ T cells. Nat Med. 1999 September; 5 (9): 1039-43.

Hegde N R, Tomazin R A, Wisner T W, Dunn C, Boname J M, Lewinsohn D M, Johnson D C. Inhibition of HLA-DR assembly, transport, and loading by human cytomegalovirus glycoprotein US3: a novel mechanism for evading major histocompatibility complex class II antigen presentation. J Virol. 2002 November; 76 (21): 10929-41.

Ahn K, Angulo A, Ghazal P, Peterson P A, Yang Y, Früh K. Human cytomegalovirus inhibits antigen presentation by a sequential multistep process. Proc Natl Acad Sci USA. 1996 Oct. 1; 93 (20): 10990-5.

Jones T R, Wiertz E J, Sun L, Fish K N, Nelson J A, Ploegh H L. Human cytomegalovirus US3 impairs transport and maturation of major histocompatibility complex class I heavy chains. Proc Natl Acad Sci USA. 1996 Oct. 15; 93 (21): 11327-33.

Ahn K, Angulo A, Ghazal P, Peterson P A, Yang Y, Früh K. Human cytomegalovirus inhibits antigen presentation by a sequential multistep process. Proc Natl Acad Sci USA. 1996 Oct. 1; 93 (20): 10990-5.

Jones T R, Wiertz E J, Sun L, Fish K N, Nelson J A, Ploegh H L. Human cytomegalovirus US3 impairs transport and maturation of major histocompatibility complex class I heavy chains. Proc Natl Acad Sci USA. 1996 Oct. 15; 93 (21): 11327-33.

Chevalier M S, Johnson D C. Human cytomegalovirus US3 chimeras containing US2 cytosolic residues acquire major histocompatibility class I and II protein degradation properties. J Virol. 2003 April; 77 (8): 4731-8.

Chevalier M S, Daniels G M, Johnson D C. Binding of human cytomegalovirus US2 to major histocompatibility complex class I and II proteins is not sufficient for their degradation. J Virol. 2002 August; 76 (16): 8265-75.

S. S. Vembar, J. L. Brodsky One step at a time: endoplasmic reticulum-associated degradation Nat. Rev. Mol. Cell Biol., 9 (2008), pp. 944-957

A. Hershko, A. Ciechanover. The ubiquitin system Annu. Rev. Biochem., 67 (1998), pp. 425-479

Lybarger, L., X. Wang, M. Harris, and T. H. Hansen. 2005. Viral immune evasion molecules attack the ER peptide-loading complex and exploit E R-associated degradation pathways. Curr. Opin. Immunol. 17:71-78.

Petersen, J. L., C. R. Morris, and J. C. Solheim. 2003. Virus evasion of MHC class I molecule presentation. J. Immunol. 171:4473-4478.

Tortorella, D., B. E. Gewurz, M. H. Furman, D. J. Schust, and H. L. Ploegh. 2000. Viral subversion of the immune system. Annu. Rev. Immunol. 18:861-926

Mocarski, E. S., Jr. 2002. Immunomodulation by cytomegaloviruses: manipulative strategies beyond evasion. Trends Microbiol. 10:332-339.

Stagg H R, Thomas M, van den Boomen D, Wiertz E J, Drabkin H A, Gemmill R M et al. The TRC8 E3 ligase ubiquitinates MHC class I molecules before dislocation from the E R. J Cell Biol 2009; 186:685-692S.

Loureiro J, Lilley B N, Spooner E, Noriega V, Tortorella D, Ploegh H L. Signal peptide peptidase is required for dislocation from the endoplasmic reticulum. Nature. 2006 Jun. 15; 441 (7095): 894-7.

Tomazin R, Boname J, Hegde N R, Lewinsohn D M, Altschuler Y, Jones T R, Cresswell P, Nelson J A, Riddell S R, Johnson D C Cytomegalovirus US2 destroys two components of the MHC class II pathway, preventing recognition by CD4+ T cells. Nat Med. 1999 September; 5 (9): 1039-43.

https://www.nature.com/articles/cmi2014105

Anne Halenius, Carolin Gerke & Hartmut Hengel Classical and non-classical MHC I molecule manipulation by human cytomegalovirus: so many targets but how many arrows in the quiver? Cellular & Molecular Immunology volume 12, pages 139-153 (2015)

Eric W Hewitt The MHC class I antigen presentation pathway: strategies for viral immune evasion. Immunology. 2003 October; 110 (2): 163-169.

What is claimed is:

1. A chimeric fusion protein comprising a target protein binding moiety comprising an anti-TCRαβ scFv, one or more transmembrane domain of a viral ER-resident glycoprotein and one or more cytoplasmic domain of a viral ER-resident glycoprotein, wherein the viral ER-resident glycoprotein comprises Adenovirus E19.

2. The chimeric fusion protein of claim 1, further comprising a hinge/linker region.

3. The chimeric fusion protein of claim 2, wherein the hinge region or the hinge is selected from the group consisting of:
   (a) an immunoglobulin hinge sequence or a functional fragment or variant thereof,
   (b) a type II C-lectin interdomain (stalk) region or a functional fragment or variant thereof, and
   (c) a cluster of differentiation (CD) molecule stalk region or a functional variant thereof.

4. The chimeric fusion protein of claim 2, wherein the linker has from one to about ten repeats of Glyx Sery, wherein x and y are independently an integer from 0 to 10 provided that x and y are not both 0.

5. The chimeric fusion protein of claim 1, further comprising a self-cleavage 2A sequence and a Chimeric Antigen Receptor (CAR), wherein the viral ER-resident glycoprotein is a full-length viral ER-resident glycoprotein.

6. The chimeric fusion protein of claim 5, wherein the CAR comprises a VH and VL portion of a scFv, a hinge attaching the scFv to the transmembrane domain, and an intracellular effector, wherein the scFv targets TAA, and the intracellular effector comprises the intracellular domain of CD3ζ.

7. The chimeric fusion protein of claim 1, further comprising a self-cleavage 2A sequence and a functional T cell Receptor (TCR), wherein the TCR includes TCR a and b chain fusion protein, coding for a CDR3 region of a TCR recognizing a tumor antigen (TAA).

8. The chimeric fusion protein of claim 1, further comprising a self-cleavage 2A sequence and chimeric NK receptor with adaptor protein fused to T cell activation signaling motif with flexible linker with or without costimulatory domain.

9. The chimeric fusion protein of claim 1, further comprising a self-cleavage 2A sequence and a chemokine receptor that helps to direct T cells toward chemokines expressed by tumors, wherein the viral ER-resident glycoprotein is a full-length viral ER-resident glycoprotein.

10. The chimeric fusion protein of claim 3, wherein the hinge region is a human IgG hinge region.

11. The chimeric fusion protein of claim 3, wherein the hinge region comprises an amino acid sequence selected from the group consisting of SEQ ID NO: 1 to SEQ ID NO: 9.

12. The chimeric fusion protein of claim 3, wherein the cluster of differentiation (CD) molecule stalk region is a natural hinge region derived from a wide-type CD molecule.

13. The chimeric fusion protein of claim 3, wherein the cluster of differentiation (CD) molecule stalk region comprises an amino acid sequence selected from the group consisting of SEQ ID NO: 10 to SEQ ID NO: 14.

14. The chimeric fusion protein of claim 2, wherein the linker comprises an amino acid sequence selected from the group consisting of (Gly4 Ser)2 (SEQ ID NO: 15) and (Gly3Ser)2 (SEQ ID NO: 16).

15. The chimeric fusion protein of claim 1, wherein the viral ER-resident glycoprotein comprises an amino acid sequence selected from the group consisting of SEQ ID NO: 16 to SEQ ID NO:31.

16. The chimeric fusion protein of claim 5, wherein the self-cleavage 2A sequence comprises an amino acid sequence selected from the group consisting of SEQ ID NO: 32 to SEQ ID NO: 35.

17. The chimeric fusion protein of claim 1, wherein the viral ER-resident glycoprotein is selected from the group consisting of HCMV US6 and HSV ICP47.

18. The chimeric fusion protein of claim 6, wherein the intracellular effector further comprises one or more co-stimulatory signaling domain fused to the intracellular domain of CD3ζ.

19. The chimeric fusion protein of claim 12, wherein the wild-type CD molecule is CD8 or CD4.

20. The chimeric fusion protein of claim 9, wherein the chemokine receptor comprises CCR4, CCR5, CCR6, CCR7, CCR9, CCR2b, CXCR1, CXCR2 or CXCR4.

* * * * *

SEQUENCE LISTING

```
<160> NUMBER OF SEQ ID NOS: 35

<210> SEQ ID NO 1
<211> LENGTH: 15
<212> TYPE: PRT
<213> ORGANISM: Artificial Sequence
<220> FEATURE:
<223> OTHER INFORMATION: synthesized

<400> SEQUENCE: 1

Glu Pro Lys Ser Cys Asp Lys Thr His Thr Cys Pro Pro Cys Pro
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: synthesized

<400> SEQUENCE: 2

Glu Arg Lys Cys Cys Val Glu Cys Pro Pro Cys Pro
1               5                   10

<210> SEQ ID NO 3
<211> LENGTH: 61
```

-continued

```
<212> TYPE: PRT
<213> ORGANISM: Artificial Sequence
<220> FEATURE:
<223> OTHER INFORMATION: synthesized

<400> SEQUENCE: 3

Leu Lys Thr Pro Leu Gly Asp Thr Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
        35                  40                  45

Lys Ser Cys Asp Thr Pro Pro Cys Pro Arg Cys Pro
    50                  55                  60

<210> SEQ ID NO 4
<211> LENGTH: 12
<212> TYPE: PRT
<213> ORGANISM: Artificial Sequence
<220> FEATURE:
<223> OTHER INFORMATION: synthesized

<400> SEQUENCE: 4

Glu Ser Lys Tyr Gly Pro Pro Cys Pro Ser Cys Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: synthesized

<400> SEQUENCE: 5

Glu Ser Lys Tyr Gly Pro Pro Cys Pro Pro Cys Pro
1               5                   10

<210> SEQ ID NO 6
<211> LENGTH: 21
<212> TYPE: PRT
<213> ORGANISM: Artificial Sequence
<220> FEATURE:
<223> OTHER INFORMATION: synthesized

<400> SEQUENCE: 6

Pro Val Pro Ser Thr Pro Pro Thr Pro Ser Pro Ser Thr Pro Pro Thr
1               5                   10                  15

Pro Ser Pro Ser Cys
            20

<210> SEQ ID NO 7
<211> LENGTH: 58
<212> TYPE: PRT
<213> ORGANISM: Artificial Sequence
<220> FEATURE:
<223> OTHER INFORMATION: synthesized

<400> SEQUENCE: 7

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Gly Arg Gly Gly Glu Glu Lys Lys Lys Glu Lys Glu Lys Glu
        35                  40                  45
```

```
Glu Gln Glu Glu Arg Glu Thr Lys Thr Pro
    50                  55

<210> SEQ ID NO 8
<211> LENGTH: 112
<212> TYPE: PRT
<213> ORGANISM: Artificial Sequence
<220> FEATURE:
<223> OTHER INFORMATION: synthesized

<400> SEQUENCE: 8

Ile Ala Glu Leu Pro Pro Lys Val Ser Val Phe Val Pro Pro Arg Asp
1               5                   10                  15

Gly Phe Phe Gly Asn Pro Arg Lys Ser Lys Leu Ile Cys Gln Ala Thr
                20                  25                  30

Gly Phe Ser Pro Arg Gln Ile Gln Val Ser Trp Leu Arg Glu Gly Lys
            35                  40                  45

Gln Val Gly Ser Gly Val Thr Thr Asp Gln Val Gln Ala Glu Ala Lys
    50                  55                  60

Glu Ser Gly Pro Thr Thr Tyr Lys Val Thr Ser Thr Leu Thr Ile Lys
65                  70                  75                  80

Glu Ser Asp Trp Leu Gly Gln Ser Met Phe Thr Cys Arg Val Asp His
                85                  90                  95

Arg Gly Leu Thr Phe Gln Gln Asn Ala Ser Ser Met Cys Val Pro Asp
            100                 105                 110

<210> SEQ ID NO 9
<211> LENGTH: 36
<212> TYPE: PRT
<213> ORGANISM: Artificial Sequence
<220> FEATURE:
<223> OTHER INFORMATION: synthesized

<400> SEQUENCE: 9

Pro Thr Val Lys Ile Leu Gln Ser Ser Cys Asp Gly Gly Gly His Phe
1               5                   10                  15

Pro Pro Thr Ile Gln Leu Leu Cys Leu Val Ser Gly Tyr Thr Pro Gly
                20                  25                  30

Thr Ile Asn Ile
        35

<210> SEQ ID NO 10
<211> LENGTH: 48
<212> TYPE: PRT
<213> ORGANISM: Artificial Sequence
<220> FEATURE:
<223> OTHER INFORMATION: synthesized

<400> SEQUENCE: 10

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
                20                  25                  30

Ala Ala Gly Gly Ala Val His Thr Arg Gly Leu Asp Phe Ala Cys Asp
            35                  40                  45

<210> SEQ ID NO 11
<211> LENGTH: 45
<212> TYPE: PRT
<213> ORGANISM: Artificial Sequence
<220> FEATURE:
```

<223> OTHER INFORMATION: synthesized

<400> SEQUENCE: 11

```
Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp
        35                  40                  45
```

<210> SEQ ID NO 12
<211> LENGTH: 38
<212> TYPE: PRT
<213> ORGANISM: Artificial Sequence
<220> FEATURE:
<223> OTHER INFORMATION: synthesized

<400> SEQUENCE: 12

```
Ser Val Val Asp Phe Leu Pro Thr Thr Ala Gln Pro Thr Lys Lys Ser
1               5                   10                  15
Thr Leu Lys Lys Arg Val Cys Arg Leu Pro Arg Pro Glu Thr Gln Lys
            20                  25                  30
Gly Pro Leu Cys Ser Pro
        35
```

<210> SEQ ID NO 13
<211> LENGTH: 36
<212> TYPE: PRT
<213> ORGANISM: Artificial Sequence
<220> FEATURE:
<223> OTHER INFORMATION: synthesized

<400> SEQUENCE: 13

```
Val Asp Phe Leu Pro Thr Thr Ala Gln Pro Thr Lys Lys Ser Thr Leu
1               5                   10                  15
Lys Lys Arg Val Cys Arg Leu Pro Arg Pro Glu Thr Gln Lys Gly Pro
            20                  25                  30
Leu Cys Ser Pro
        35
```

<210> SEQ ID NO 14
<211> LENGTH: 23
<212> TYPE: PRT
<213> ORGANISM: Artificial Sequence
<220> FEATURE:
<223> OTHER INFORMATION: synthesized

<400> SEQUENCE: 14

```
Asp Ser Gly Gln Val Leu Leu Glu Ser Asn Ile Lys Val Leu Pro Thr
1               5                   10                  15
Trp Ser Thr Pro Val Gln Pro
            20
```

<210> SEQ ID NO 15
<211> LENGTH: 5
<212> TYPE: PRT
<213> ORGANISM: Artificial Sequence
<220> FEATURE:
<223> OTHER INFORMATION: synthesized

<400> SEQUENCE: 15

```
Gly Gly Gly Gly Ser
1               5
```

```
<210> SEQ ID NO 16
<211> LENGTH: 10
<212> TYPE: PRT
<213> ORGANISM: Artificial Sequence
<220> FEATURE:
<223> OTHER INFORMATION: synthesized

<400> SEQUENCE: 16

Gly Gly Gly Gly Ser Gly Gly Gly Gly Ser
1               5                   10

<210> SEQ ID NO 17
<211> LENGTH: 8
<212> TYPE: PRT
<213> ORGANISM: Artificial Sequence
<220> FEATURE:
<223> OTHER INFORMATION: synthesized

<400> SEQUENCE: 17

Gly Gly Gly Ser Gly Gly Gly Ser
1               5

<210> SEQ ID NO 18
<211> LENGTH: 21
<212> TYPE: PRT
<213> ORGANISM: Artificial Sequence
<220> FEATURE:
<223> OTHER INFORMATION: synthesized

<400> SEQUENCE: 18

Val Ala Trp Thr Ile Val Phe Tyr Ser Ile Asn Ile Thr Leu Leu Val
1               5                   10                  15

Leu Phe Ile Val Tyr
            20

<210> SEQ ID NO 19
<211> LENGTH: 21
<212> TYPE: PRT
<213> ORGANISM: Artificial Sequence
<220> FEATURE:
<223> OTHER INFORMATION: synthesized

<400> SEQUENCE: 19

Thr Leu Leu Val Tyr Leu Phe Ser Leu Val Val Leu Val Leu Leu Thr
1               5                   10                  15

Val Gly Val Ser Ala
            20

<210> SEQ ID NO 20
<211> LENGTH: 21
<212> TYPE: PRT
<213> ORGANISM: Artificial Sequence
<220> FEATURE:
<223> OTHER INFORMATION: synthesized

<400> SEQUENCE: 20

Thr Leu Leu Val Tyr Leu Phe Ser Leu Val Val Leu Val Leu Leu Thr
1               5                   10                  15

Val Gly Val Ser Ala
            20

<210> SEQ ID NO 21
<211> LENGTH: 5
<212> TYPE: PRT
```

<210> SEQ ID NO 21
<211> LENGTH: 5
<212> TYPE: PRT
<213> ORGANISM: Artificial Sequence
<220> FEATURE:
<223> OTHER INFORMATION: synthesized

<400> SEQUENCE: 21

Arg Leu Arg Phe Ile
1               5

<210> SEQ ID NO 22
<211> LENGTH: 21
<212> TYPE: PRT
<213> ORGANISM: Artificial Sequence
<220> FEATURE:
<223> OTHER INFORMATION: synthesized

<400> SEQUENCE: 22

Tyr Thr Leu Met Met Val Ala Val Ile Gln Val Phe Trp Gly Leu Tyr
1               5                   10                  15

Val Lys Gly Trp Leu
            20

<210> SEQ ID NO 23
<211> LENGTH: 12
<212> TYPE: PRT
<213> ORGANISM: Artificial Sequence
<220> FEATURE:
<223> OTHER INFORMATION: synthesized

<400> SEQUENCE: 23

His Arg His Phe Pro Trp Met Phe Ser Asp Gln Trp
1               5                   10

<210> SEQ ID NO 24
<211> LENGTH: 21
<212> TYPE: PRT
<213> ORGANISM: Artificial Sequence
<220> FEATURE:
<223> OTHER INFORMATION: synthesized

<400> SEQUENCE: 24

Leu Gly Asp Tyr Gly Ala Ile Leu Lys Ile Tyr Phe Gly Leu Phe Cys
1               5                   10                  15

Gly Ala Cys Val Ile
            20

<210> SEQ ID NO 25
<211> LENGTH: 15
<212> TYPE: PRT
<213> ORGANISM: Artificial Sequence
<220> FEATURE:
<223> OTHER INFORMATION: synthesized

<400> SEQUENCE: 25

Thr Arg Ser Leu Leu Leu Ile Cys Gly Tyr Tyr Pro Pro Arg Glu
1               5                   10                  15

<210> SEQ ID NO 26
<211> LENGTH: 21
<212> TYPE: PRT
<213> ORGANISM: Artificial Sequence
<220> FEATURE:
<223> OTHER INFORMATION: synthesized

<400> SEQUENCE: 26

Phe Phe Ala Val Thr Leu Tyr Leu Cys Cys Gly Ile Thr Leu Leu Val
1               5                   10                  15

Val Ile Leu Ala Leu
            20

<210> SEQ ID NO 27
<211> LENGTH: 18
<212> TYPE: PRT
<213> ORGANISM: Artificial Sequence
<220> FEATURE:
<223> OTHER INFORMATION: synthesized

<400> SEQUENCE: 27

Leu Cys Ser Ile Thr Tyr Glu Ser Thr Gly Arg Gly Ile Arg Arg Cys
1               5                   10                  15

Gly Ser

<210> SEQ ID NO 28
<211> LENGTH: 21
<212> TYPE: PRT
<213> ORGANISM: Artificial Sequence
<220> FEATURE:
<223> OTHER INFORMATION: synthesized

<400> SEQUENCE: 28

Thr Phe Cys Ser Thr Ala Leu Leu Ile Thr Ala Leu Ala Leu Val Cys
1               5                   10                  15

Thr Leu Leu Tyr Leu
            20

<210> SEQ ID NO 29
<211> LENGTH: 15
<212> TYPE: PRT
<213> ORGANISM: Artificial Sequence
<220> FEATURE:
<223> OTHER INFORMATION: synthesized

<400> SEQUENCE: 29

Lys Tyr Lys Ser Arg Arg Ser Phe Ile Asp Glu Lys Lys Met Pro
1               5                   10                  15

<210> SEQ ID NO 30
<211> LENGTH: 21
<212> TYPE: PRT
<213> ORGANISM: Artificial Sequence
<220> FEATURE:
<223> OTHER INFORMATION: synthesized

<400> SEQUENCE: 30

Ala Ile Val Ala Leu Val Val Ala Ile Ile Ile Ala Ile Val Val Trp
1               5                   10                  15

Ser Ile Val Ile Ile
            20

<210> SEQ ID NO 31
<211> LENGTH: 54
<212> TYPE: PRT
<213> ORGANISM: Artificial Sequence
<220> FEATURE:
<223> OTHER INFORMATION: synthesized

<400> SEQUENCE: 31

Glu Tyr Arg Lys Ile Leu Arg Gln Arg Lys Ile Asp Arg Leu Ile Asp
1               5                   10                  15

Arg Leu Ile Glu Arg Ala Glu Asp Ser Gly Asn Glu Ser Glu Gly Glu
            20                  25                  30

```
Ile Ser Ala Leu Val Glu Met Gly Val Glu Met Gly His His Ala Pro
            35                  40                  45

Trp Asp Val Asp Asp Leu
    50

<210> SEQ ID NO 32
<211> LENGTH: 21
<212> TYPE: PRT
<213> ORGANISM: Artificial Sequence
<220> FEATURE:
<223> OTHER INFORMATION: synthesized

<400> SEQUENCE: 32

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 33
<211> LENGTH: 22
<212> TYPE: PRT
<213> ORGANISM: Artificial Sequence
<220> FEATURE:
<223> OTHER INFORMATION: synthesized

<400> SEQUENCE: 33

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 34
<211> LENGTH: 23
<212> TYPE: PRT
<213> ORGANISM: artificial sequence
<220> FEATURE:
<223> OTHER INFORMATION: synthesized

<400> SEQUENCE: 34

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 35
<211> LENGTH: 25
<212> TYPE: PRT
<213> ORGANISM: Artificial Sequence
<220> FEATURE:
<223> OTHER INFORMATION: synthesized

<400> SEQUENCE: 35

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```